(12) United States Patent
Li et al.

(10) Patent No.: US 12,089,952 B2
(45) Date of Patent: Sep. 17, 2024

(54) FOOT SENSOR AND OTHER SENSOR PADS

(71) Applicant: Xsensor Technology Corporation, Calgary (CA)

(72) Inventors: Jeffrey Chao-Hsin Li, Calgary (CA); John Alexander Hogg, Calgary (CA); Adele Syt Fu Chui, Calgary (CA)

(73) Assignee: Xsensor Technology Corporation, Calgary (CA)

( * ) Notice: Subject to any disclaimer, the term of this patent is extended or adjusted under 35 U.S.C. 154(b) by 453 days.

(21) Appl. No.: 17/387,387

(22) Filed: Jul. 28, 2021

(65) Prior Publication Data

US 2022/0031241 A1 Feb. 3, 2022

Related U.S. Application Data

(60) Provisional application No. 63/057,546, filed on Jul. 28, 2020.

(51) Int. Cl.
*A61B 5/00* (2006.01)
*A43B 3/34* (2022.01)
(Continued)

(52) U.S. Cl.
CPC .............. *A61B 5/6802* (2013.01); *A43B 3/34* (2022.01); *A43B 3/44* (2022.01); *A43B 3/48* (2022.01); *A43B 17/00* (2013.01); *A61B 5/0002* (2013.01); *A61B 5/6807* (2013.01); *A61B 5/743* (2013.01); *G01L 1/146* (2013.01); (Continued)

(58) Field of Classification Search
CPC .............................. A43B 17/00; A61B 5/6807
See application file for complete search history.

(56) References Cited

U.S. PATENT DOCUMENTS 3,565,195 A 2/1971 Miller et al.
3,826,926 A 7/1974 White et al.
(Continued)

FOREIGN PATENT DOCUMENTS

CN 205795032 U * 12/2016 ............. A43B 17/00
CN 109443611 A * 3/2019
(Continued)

OTHER PUBLICATIONS

XSENSOR Technology Corporation, "Introducing X4 Foot and Gait Measurement System"; uploaded Sep. 13, 2019; video length 2:01 (web address: https://www.youtube.com/watch?v=a10TdB0wLeE) (Year: 2019).*

*Primary Examiner* — Ryan D Walsh
(74) *Attorney, Agent, or Firm* — Fenwick & West LLP (57) ABSTRACT

The enclosed describes a sensor pad for wearing on a human body. The sensor pad is configured to be in contact with a substrate having a contoured surface, such as a surface of the body. The sensor pad comprises at least a sensor layer and a stiffener layer. The sensor layer comprises a surface area defining a sensing area configured to measure value at a plurality of locations of the sensing area. The stiffener layer is couples to the surface area of the sensor layer. The stiffener layer has a micro-cut pattern to reduce mechanical resistance of the stiffener layer. The micro-cut pattern facilitates the stiffener layer in stretching or compressing in one or more predefined directions, enabling the stiffener lay to conform to the contoured surface of the substrate.

20 Claims, 10 Drawing Sheets

(51) Int. Cl.
    *A43B 3/44* (2022.01)
    *A43B 3/48* (2022.01)
    *A43B 17/00* (2006.01)
    *G01L 1/14* (2006.01)
(52) U.S. Cl.
    CPC ............... *A61B 2562/0247* (2013.01); *A61B 2562/0271* (2013.01); *A61B 2562/164* (2013.01); *A61B 2562/227* (2013.01)

(56) References Cited

U.S. PATENT DOCUMENTS

| | | | |
|---|---|---|---|
| 3,875,481 | A | 4/1975 | Miller et al. |
| 4,005,438 | A | 1/1977 | Meltzer et al. |
| 4,266,263 | A | 5/1981 | Haberl et al. |
| 4,370,697 | A | 1/1983 | Haberl et al. |
| 4,584,625 | A | 4/1986 | Kellogg |
| 4,986,136 | A | 1/1991 | Brunner et al. |
| 5,010,772 | A | 4/1991 | Bourland et al. |
| 5,033,291 | A * | 7/1991 | Podoloff ............... G01L 1/205 73/172 |
| 5,306,912 | A | 4/1994 | Sibbald et al. |
| 5,401,922 | A | 3/1995 | Asta |
| 5,447,076 | A | 9/1995 | Ziegler |
| 5,514,832 | A | 5/1996 | Dusablon et al. |
| 5,653,939 | A | 8/1997 | Hollis et al. |
| 5,693,886 | A | 12/1997 | Seimiya et al. |
| 6,195,921 | B1 * | 3/2001 | Truong ............... A43B 3/00 36/137 |
| 6,826,968 | B2 | 12/2004 | Manaresi et al. |
| 7,067,979 | B2 | 6/2006 | Sakamoto |
| 7,580,030 | B2 | 8/2009 | Marten |
| 7,609,178 | B2 | 10/2009 | Son et al. |
| 7,638,350 | B2 | 12/2009 | Deconde et al. |
| 8,272,276 | B2 | 9/2012 | Gorjanc et al. |
| 8,893,561 | B2 | 11/2014 | Gorjanc et al. |
| 9,587,991 | B2 * | 3/2017 | Padiy ............... A61B 5/01 |
| 9,860,982 | B1 * | 1/2018 | Main ............... H05K 1/09 |
| 2003/0182821 | A1 * | 10/2003 | Chen ............... A43B 17/16 36/44 |
| 2004/0133092 | A1 | 7/2004 | Kain |
| 2006/0070260 | A1 * | 4/2006 | Cavanagh ............... G16H 50/50 36/44 |
| 2008/0180390 | A1 | 7/2008 | Yoshikawa |
| 2008/0306410 | A1 * | 12/2008 | Kalpaxis ............... A61B 5/0002 600/592 |
| 2012/0323501 | A1 * | 12/2012 | Sarrafzadeh ............... G01L 1/18 702/41 |
| 2016/0287937 | A1 * | 10/2016 | Fitzgerald ............ G09B 19/0038 |
| 2017/0188950 | A1 * | 7/2017 | Gazdag ............... G16H 20/30 |
| 2019/0283394 | A1 * | 9/2019 | Ashcroft ............... A43D 1/02 |

FOREIGN PATENT DOCUMENTS

| | | | | |
|---|---|---|---|---|
| CN | 111631486 | A * | 9/2020 | |
| CN | 111741693 | A * | 10/2020 | ............ A43B 13/14 |
| KR | 20110087710 | A * | 8/2011 | |
| WO | WO-9415530 | A1 * | 7/1994 | ............ A43B 3/0005 |
| WO | WO-9718450 | A1 * | 5/1997 | ............ A61B 5/1036 |
| WO | WO-2007021328 | A1 * | 2/2007 | ............ A43B 13/188 |
| WO | WO-2009089406 | A2 * | 7/2009 | ............ A43B 17/00 |
| WO | WO-2017079628 | A1 * | 5/2017 | ............ A43B 3/0005 |
| WO | WO-2021092676 | A1 * | 5/2021 | ............ A43B 3/0005 |

* cited by examiner

FOOT SENSOR AND OTHER SENSOR PADS

CROSS REFERENCE TO RELATED APPLICATIONS

This application claims the benefit of the U.S. Provisional Patent Application No. 63/057,546 filed on Jul. 28, 2020, which is incorporated by reference for all purposes. U.S. Pat. No. 8,272,276, patented on Sep. 25, 2012, entitled "Dielectric Textured Elastomer in a Pressure Mapping System" is also incorporated by reference for all purposes.

TECHNICAL FIELD

The disclosed embodiments generally relate to wearable sensors.

BACKGROUND

Due to the contoured surface and soft texture of the human body, taking accurate sensor readings of some portions of the body can be difficult. The curvature of surfaces of the human body renders rigid sensors ineffective as they cannot conform properly. Further, surfaces of the human body that one may want to take sensor readings of are frequently in contact with other contoured surfaces. For example, foot or hand sensing may be additionally complicated by the surface of a shoe or glove. As such, the human body is best measured with flexible sensors. However, flexible sensors may incur issues of their own such as bunching, folding, or movement of the sensor against the surface of the human body causing inaccurate readings.

SUMMARY

In some embodiments, a wearable sensor pad configured to be in contact with a surface of the human body is described. The sensor pad includes several layers including a sensing layer capable of detecting temperature, pressure, or other values via a capacitance sensor or other sensing mechanism. The sensing layer has multiple discrete sensing locations at which values can be detected. The sensing layer is supported by a stiffener layer that prevents the sensing layer from folding and harming electrical connections within. The stiffener layer is etched, cut, or otherwise marked with a micro-cut pattern. The micro-cut pattern reduces resistance of the stiffener layer and enables the stiffener layer to compress, stretch, or bend in a predefined direction and may cover all or a portion of the surface area of the stiffener layer.

In one embodiment, the wearable sensor takes the form of an insole for a shoe that uses a capacitive sensor. In this embodiment, the wearable sensor is shaped to fit into a shoe and match the contours of a foot. The capacitive sensor comprises two conductive layers surrounding a dielectric layer such that as a foot applies pressure to the sensor pad the layers are pushed together, varying the capacitance at the multiple sensing locations.

In some embodiments, the sensor pad has additional layers that may include a flexible enclosure of fabric or flexible materials that encapsulate the layers of the sensor and protect the interior layers. Other components of the sensor pad include perimeter stiffeners, wiring, and friction pads. The perimeter stiffeners are configured along the side of the sensor pad, away from the sensing area. The perimeter stiffeners provide locations at which the sensor pad can be folded to fit into a shoe while also protecting the wires along the perimeter of the sensing area (e.g., peripheral region) from being bent. The friction pads are also along areas of the sensor pad that are meant to be folded. The friction pads are configured to have a rough texture such that they increase friction between the sensor pad and the surface it is coupled to, such as the inside of a shoe.

In some embodiments, the electrical portion of the sensor pad includes two conductive layers, each layer having a series of wires. The series of wires on the two conductive layers run along different directions (e.g. non-parallel to each other) such that when the two conductive layers are overlayed the wires intersect at multiple locations, these locations being the sensing locations. The values at the sensing location are conducted through wires in the peripheral region through an electrical connector. The electrical connector may be attached to a wireless transmitter that enables the values to be communicated to a server or application.

In some embodiments, the sensor pad has an associated application with a user interface. The user interface of the application displays a visualization of the sensing values of the sensor pad. For example, in the embodiment of the sensor pad being an insole, the user interface may depict a pressure heat map or a gait graph.

The features and advantages described in this summary and the following detailed description are not all-inclusive. Many additional features and advantages will be apparent to one of ordinary skill in the art in view of the drawings, specification, and claims hereof.

The figures depict various embodiments of the present invention for purposes of illustration only. One skilled in the art will readily recognize from the following description that other alternative embodiments of the structures and methods illustrated herein may be employed without departing from the principles of the invention described herein.

DETAILED DESCRIPTION

Various embodiments of wearable sensor pads are described in detail below. The wearable sensor pad may exist in a network environment in which it is connected, through a wireless transmitter, to a network. The network further enables connection of the sensor pad to a server and application on which data gathered by the sensor pad can be processed, stored, and visualized. The sensor pad comprises several layers including a flexible enclosure, shielding layer, stiffener layer, conductive grid, dielectric, wiring, and perimeter stiffeners. Together the layers comprise a sensor pad capable of being conformed to contoured surfaces for comfortable wear and accurate sensing on the human body.

The figures (FIGs.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Example System Environment

Figure 1:
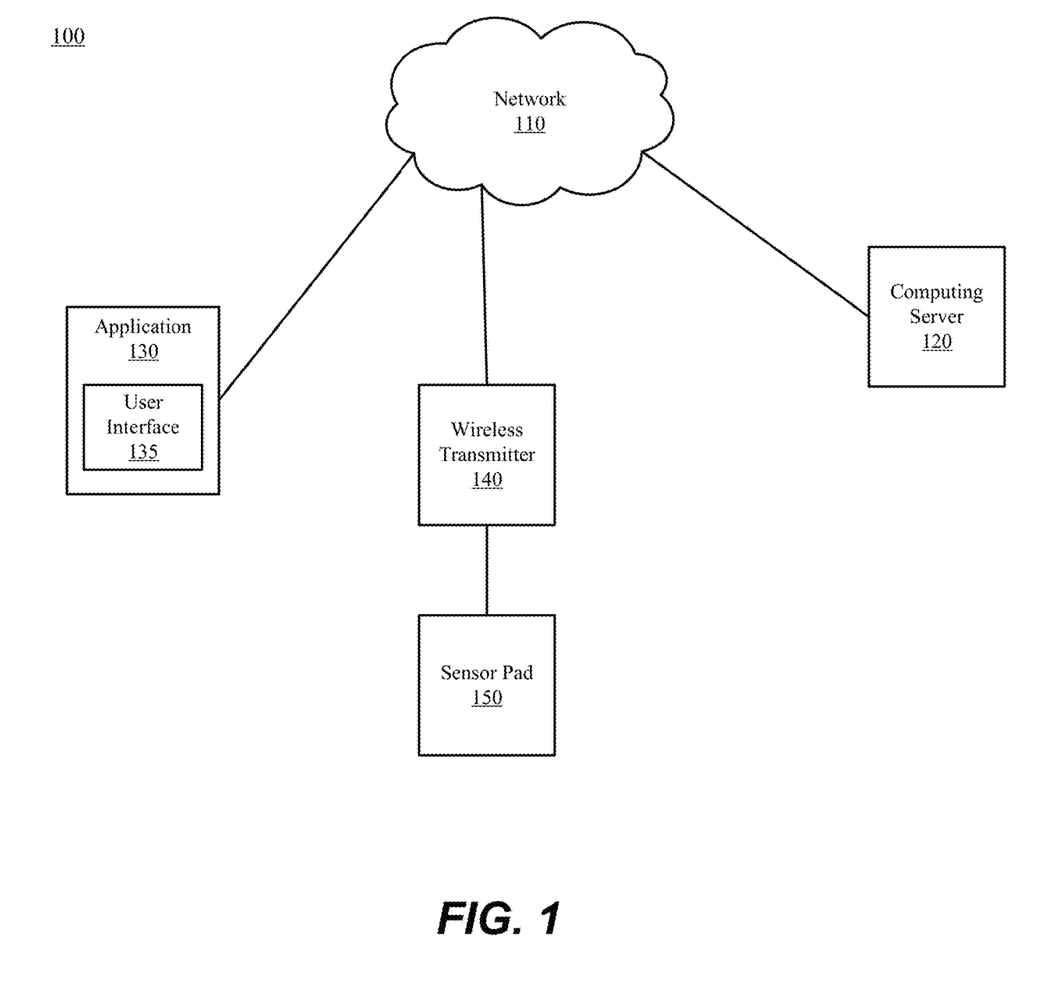
FIG. 1 is a block diagram illustrating an example sensor system, in accordance with some embodiments.

FIG. 1 is a block diagram illustrating an example system 100 in which the sensor pad 150 operates, in accordance with some embodiments. The system 100 includes network 110, a computing server 120, an application 130 with user interface 135, a wireless transmitter 140, and the sensor pad 150. The sensor pad 150 gathers sampled values or signals and transmits them to the network 110 via the wireless transmitter 140. In various embodiments, the system 100 includes fewer and additional components that are not shown in FIG. 1.

While some of the components in the environment 100 may at times be described in a singular form while other components may be described in a plural form, the environment 100 may include one or more of each of the components. For simplicity, multiple instances of a type of entity or component in the environment 100 may be referred to in a singular form even though the system may include one or more such entities or components. Conversely, a component described in the plural form does not necessarily imply that more than one copy of the component is always needed in the environment 100.

The network 110 may include any combination of local area and/or wide area networks using both wireless and/or wired communication systems. For example, the network 110 may include the Internet, as well as mobile telephone networks. In one embodiment, the network 110 uses standard communications technologies and/or protocols. Hence, the network 110 may include links using technologies such as Ethernet, 802.11, worldwide interoperability for microwave access (WiMAX), 2G/3G/4G mobile communications protocols, digital subscriber line (DSL), asynchronous transfer mode (ATM), InfiniBand, PCI Express Advanced Switching, etc. Similarly, the networking protocols used on the network 110 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), etc. The data exchanged over the network 110 can be represented using technologies and/or formats including image data in binary form (e.g. Portable Network Graphics (PNG)), hypertext markup language (HTML), extensible markup language (XML), etc. In addition, all or some of links can be encrypted using conventional encryption technologies such as secure sockets layer (SSL), transport layer security (TLS), virtual private networks (VPNs), Internet Protocol security (IPsec), etc.

The computing server 120 stores data associated with the sensor pad 150 and may perform signal processing, data analysis, machine learning, and other prediction and inference processes interpreting data generated by the sensor pad 150. For example, the computing server 120 may store biographical data of the user of the sensor pad 150, the biographical data input to the application 130. The server may also store a history of values detected by the sensor pad 150 which can be used to portray change over time in the user interface 135. The computing server 120 is further configured to process raw data from the sensor pad and perform data analysis to make the data fit for display by the user interface 135 of the application 130.

The application 130 may be hosted on a client device such as a smart phone, tablet, laptop, or other computer. The application 130 may be a platform that enables health tracking with sensors like the wearable sensor pad 150. In one embodiment the application 130 may be in communication with multiple sensors.

In various embodiments the application 130 may take different forms. In one embodiment, the application 130 is a web application or a mobile application. In one embodiment, an application 130 is a web application that runs on JavaScript or other alternatives, such as TypeScript, etc. In the case of a web application, the application 130 may cooperate with a web browser, which is an example of user interface 135, to render the visual elements and interactive fields of the application 130. In another case, an application 130 is a mobile application. For example, the mobile application runs on Swift for iOS and other APPLE operating systems or on Java or another suitable language for ANDROID systems. In yet another case, an application 130 is a software program that operates on a desktop operating system such as LINUX, MICROSOFT WINDOWS, MAC OS, or CHROME OS.

In one embodiment, the computing server 120 manages and provides the application 130. For example, the company operating the computing server 120 may be a cloud service provider that provides a front-end software application that can be installed, run, or displayed at a client device. For example, the company provides the applications 130 as a form of software as a service (SaaS). In one case, an example application 130 is published and made available by the company operating the computing server 120 at an application store (e.g. App store) of a mobile operating system.

The user interfaces 135 may be any suitable interfaces for receiving inputs from users and for communication with users. The user interfaces 135 may take different forms. In one embodiment, the user interface 135 is a web browser such as CHROME, FIREFOX, SAFARI, INTERNET EXPLORER, EDGE, etc. and the application 135 is a web application that is run by the web browser. In another application, the user interface 135 is part of the application 130. For example, the user interface 135 is the front-end component of a mobile application or a desktop application. The user interface 135 also may be referred to as a graphical user interface (GUI) which includes graphical elements to display various elements of the application 130. In another embodiment, the user interface 135 may not include graphical elements but communicates with the computing server 120 via other suitable ways such as application program interfaces (APIs).

The computing server 120 is one or more computing devices that process inputs from users and generate various results. In this disclosure, the servers 120 may collectively and singularly be referred to as a computing server 120, even though the computing server 120 may include more than one computing device. For example, the computing server 120 is a pool of computing devices located at the same geographical location (e.g., a server room) or distributed geographically (e.g., cloud computing, distributed computing, or in a virtual server network). In some embodiments, the entity operating the computing server 120 may be the publisher of the application 130, which communicates with the computing server 120 to download various data generated by the computing server 120.

A computing device of the computing server 120 takes the form of software, hardware, or a combination thereof. For example, parts of the computing server 120 may be a PC, a tablet PC, a smartphone, an interne of things (IoT) appliance, or any machine capable of executing instructions that specify actions to be taken by that machine. Parts of the computing server 120 may include one or more processing units (e.g., a central processing unit (CPU), a graphics processing unit (GPU), a digital signal processor (DSP), a controller, a state machine, one or more ASICs, one or more RFICs, or any combination of these) and a memory.

The wireless transmitter 140 receives data from the sensor pad and transmits it to the network 110 wirelessly. The wireless transmitter 140 may, for example, be a Bluetooth, WiFi, IR, or radio transmitter. In some embodiments the transmitter 140 may be a transceiver capable of both sending and receiving data from the network 110. The wireless transmitter 140 may be physically connected to the sensor pad 150, such as being a hardware component of the sensor pad 150. For example, the wearable sensor pad 150 has an electrical connector that can be removably connected to a wireless transmitter 140. The wireless transmitter 140 transmits signals generated by a sensor layer enclosed within a flexible enclosure of the wearable sensor pad. In an example, the wireless transmitter 140 may be part of the circuitry of the sensor pad 150.

The sensor data generated by the sensor pad 150 may be processed in various ways, depending on embodiments. In one embodiment, the sensor pad 150 may upload the sensor data to the computing server 120, which performs data processing and analysis and saves historical data in a data store. In another embodiment, the sensor pad 150 may be paired with a client device that operates the application 130. For example, the sensor pad 150 may be paired, via BLUETOOTH, with a smart phone that is installed with a mobile application 130. The client device receives the data from the sensor pad 150 and uploads the data to the computing server 120. The application 130 may perform real-time data analysis and upload the data to the computing server 120 for further analysis. In some embodiments, the client device 130 may perform all data analysis without the use of a computing server 120. The historical data collected may be uploaded to a cloud data store.

Example User Interface

Figure 2:
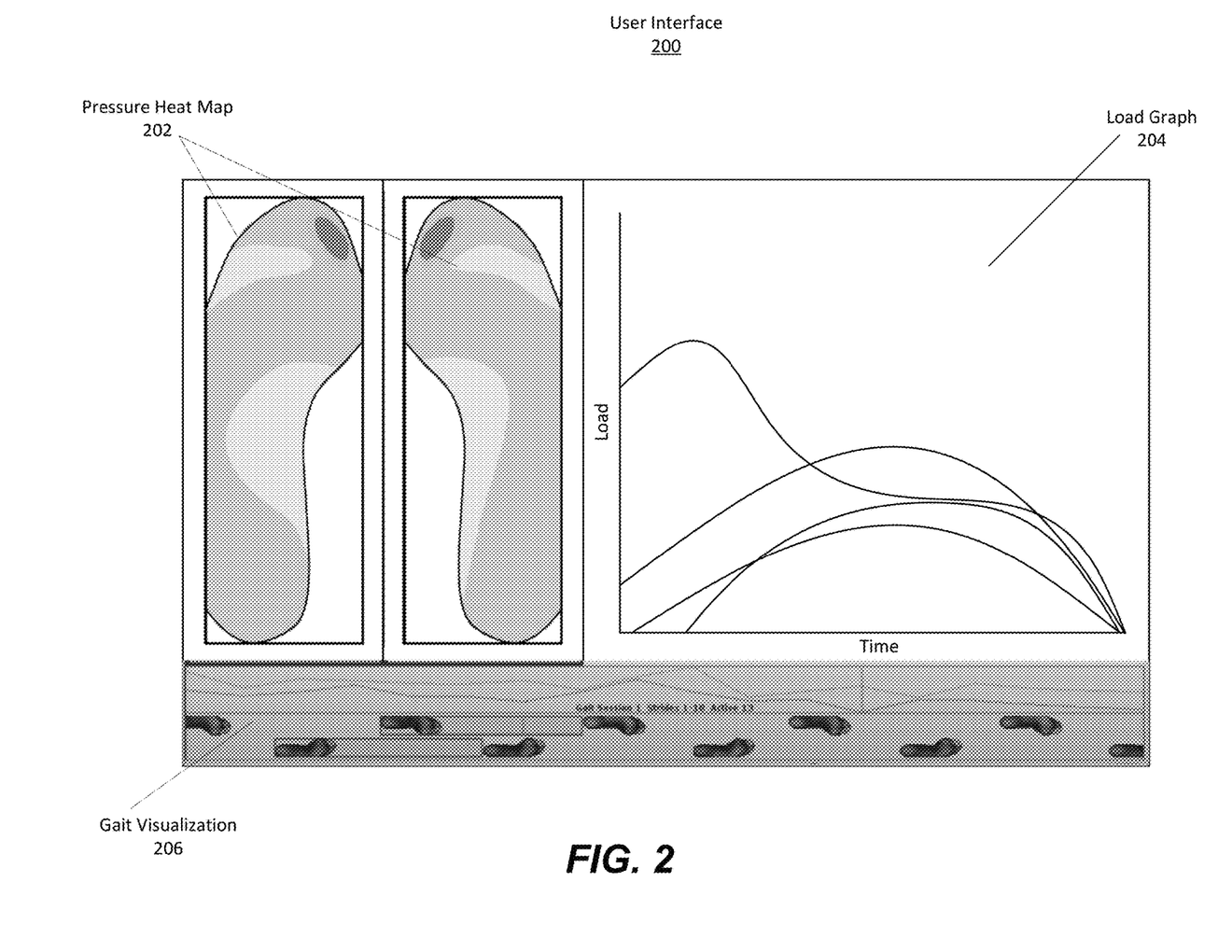
FIG. 2 is a conceptual diagram illustrating an example user interface displaying sensor pad data, in accordance with some embodiments.

FIG. 2. is a conceptual diagram illustrating a user interface 200 associated with the sensor pad 150, in accordance with some embodiments. The user interface 200 is an example embodiment of user interface 135 in the system 100. The user interface 200 displays several visualizations of the data gathered by the sensor pad and processed by the computing server 120 or application 130. For example, the sensor layer may include capacitive sensors that measure capacitance values that are proportional to the pressure exerted on the sensor pad 150 at various locations. The capacitance values may be processed and analyzed by the computing server 120 or application 130. The processed data may be displayed as heatmaps 202 to demonstrate the pressure differential at various locations of the foot when a person walks or stands. The shaded areas of the heat map 202 having the same color represent the same approximate pressure. Darker shades may indicate higher pressure. In the shown embodiment of heat map 202, there is a zone of higher pressure around the person's big toe and a zone of low pressure around the arch of the foot.

The application may also have other forms of data visualization. The application may further provide analysis of the person's gait such as a gait visualization 206 demonstrating the placement of the person's steps relative to each other. The gait visualization 206 may also include the changes in pressure readings in left foot and right foot over time to illustrate the stride pattern of the person. The user interface 200 may also include other metrics and statistics related to the person's grit, such as stride time, stride rate, step time, step rate, swing time, support time, swing and stance proportion, etc.

The user interface 200 may also illustrate the change of pressure or other variables over time based on data as recorded by the computing server 120. This recorded data is displayed in the load graph 204. The load graph 204 depicts several lines that vary in loading as time changes. Each line may, for example, represent a different area of the sensor pad (e.g. a different area of the foot), such as left or right toe, metatarsal, midfoot, and heel. The timeline may be scaled to zoom in to how the loading changes across the foot when the user takes a single step, or the timeline may be lengthened to see a change in loading of specific areas across a whole day of walking. In some embodiments, the lines of the load graph 204 may represent the readings of different sensors on the user's body. For example, the user may wear a sensor pad in both shoes and the loading graph 204 may compare the relative loading of each foot. The user interface may also include one or more data tables (not shown in FIG. 2) that shows the pressure reading, statistics, and other metrics such as the average pressure, peak pressure, time of peak pressure, average load, peak load, time of peak load, and contact area size that are derived from the sensor data.

The application 130 may additionally provide various analyses and features such as gait lines, cyclograms, foot zones, graph pressure, contact area, load, automatic stance detection, frame or stance review, "runway" view, gait & stance statistics, cadence of steps, distance traveled, steps taken and average stances.

Wearable Sensor Pad

Figure 3:
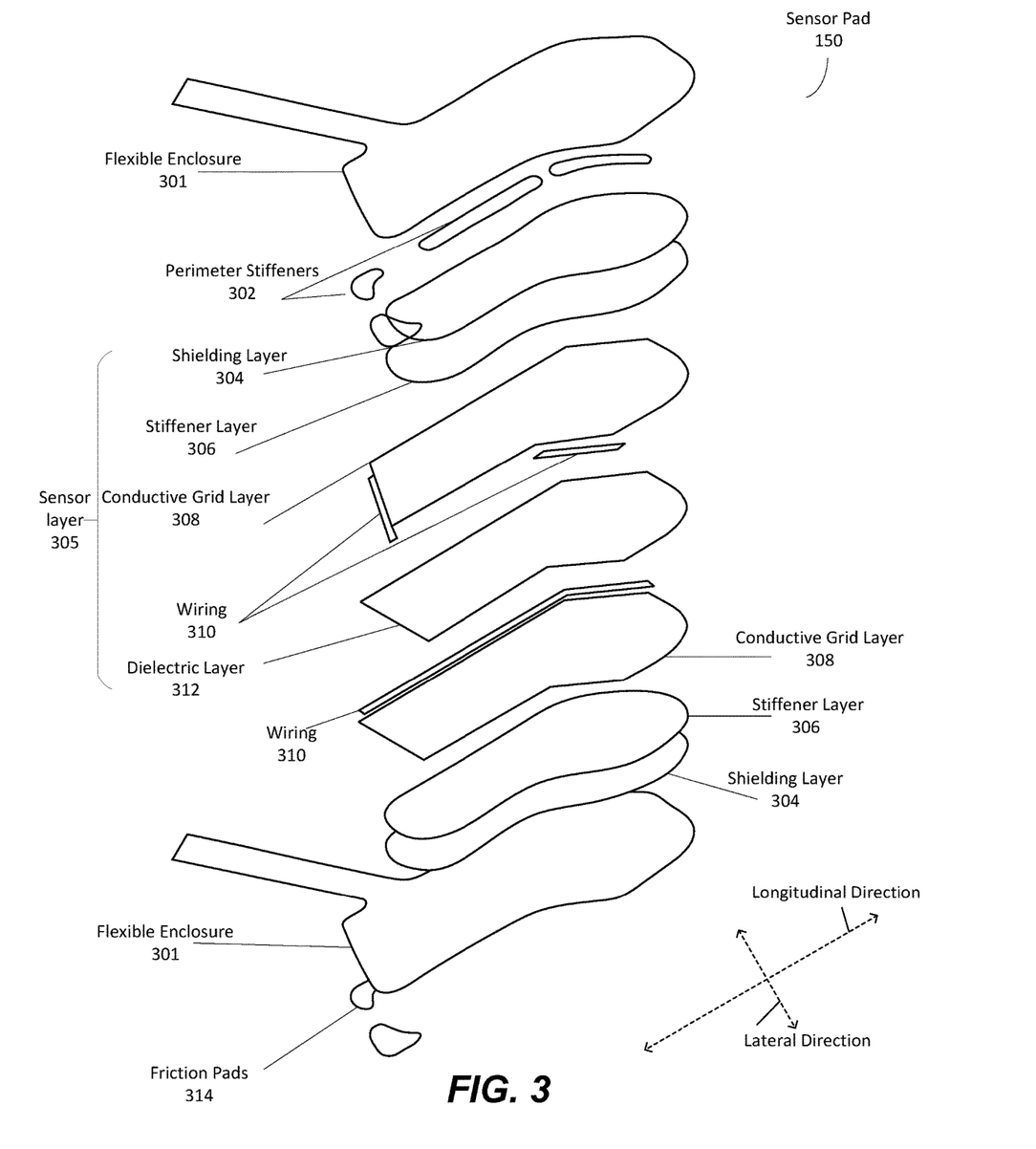
FIG. 3 is an exploded view of a sensor pad, in accordance with some embodiments.

FIG. 3 is an exploded view of the layers of the sensor pad 150, in accordance with some embodiments. The particular example of wearable sensor pad shown in FIG. 3 is an insole, but other wearable pads with various structures and features disclosed herein are also possible in various embodiments. Two layers of cover fabric form a flexible enclosure 301 that encloses the internal layers. A sensor layer 305 may include several sub-layers. For example, the sensor layer in FIG. 3 includes a grid capacitance sensor that includes two conductive grid layers 308 sandwiching a dielectric layer 312. The perimeter stiffeners 302 are rigid stiffeners that restrict and define the folding pattern of the wearable sensor pad 150. The sensing area stiffener layers 306 and the shielding layers 304 may have micro-cuts that allow the sensor layer to better conform with the potential contoured surface of the shoe floor. The friction pads 314 are located at one or more fold-up regions of the wearable sensor pad 150. The friction pads 314 can be frictionally coupled to the interior wall of a shoe. Conductive shielding layers 304 may be bonded to the stiffener layer to prevent sensor coupling, noise, and offsets. The shielding layers 304 prevent the capacitance sensor from coupling with other objects.

The sensor layer may include one or more capacitive sensors or other suitable sensors such as pressure sensors, resistive sensors, inductive sensors, piezoelectric sensors. While capacitive sensors are used as examples, the disclosure is not limited to capacitive sensors. The sensor layer can be associated with a sensor grid structure that measures different sensor values at various location of a sensing area defined by the sensor grid structure. The sensor layer generates sensor signals that are transmitted to the data processing server for processing and analysis. The sensor signals may be sampled at a certain rate (e.g., 150 fps).

Perimeter stiffeners 302, stiffener layers 304, and friction pads 314 control how the sensor may be bent as other materials in the layer stackup are more flexible. This allows the electrical bonds to bend up and away from the sensing area while also forming a heel cup when the insole is inserted into a shoe. Frictions pads 314 are on peripheral tabs which can be bent up away from the sensing area when the insole is inserted into a shoe. In this configuration, the friction pads are facing the walls of the shoe at the heel and assist in securing the sensor's position.

Stiffener layer 306 and shielding 304 may be bonded. Micro-cuts are applied to the bonded materials allowing for flexibility which can be controlled by varying the micro-cut density and pattern. Example patterns of the micro-cuts are described further in FIGS. 6 and 7. The stack is also of low compressibility to prevent any interference with pressure transmission to the sensor.

Stiffener layers 306 prevent slippage of sensing elements in shoe. The stiffener layers 306 are bonded to at least a majority of the surface area of the sensor layer. The stiffener layers 306 prevent wrinkles and creasing, allowing the sensor pad 150 to stick better to the shoe floor when in motion rather than to the user's foot which improves comfort. By ensuring the sensor pad 150 remains stationary to the shoe rather than the foot, the wearable sensor pad is less perceptible to the wearer.

The sensor layer may include sub-layers such as two layers of conductive grids. The conductive grid layers may include parallel conductive lines which are each bonded to a wire conductor at one end. The grid forms a number of sensing locations, each of which can take an independent measurement of sensor values. The wearable sensor pad transmits the sensor values to a data processing server to generate a heatmap that can be displayed at a GUI.

Figure 4:
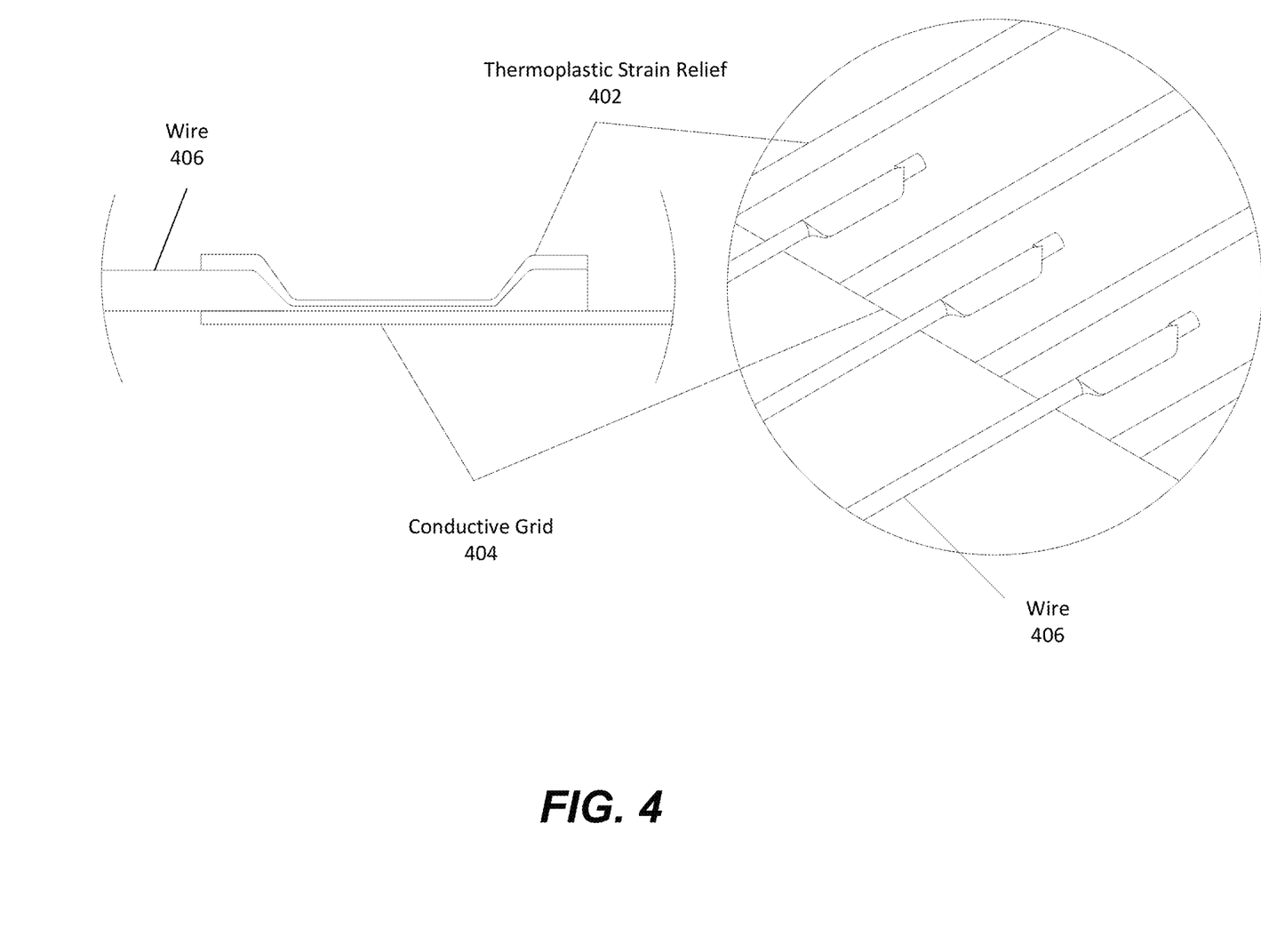
FIG. 4 is a zoomed-in view of a conductive grid in a sensor pad, in accordance with some embodiments.

FIG. 4 is a zoomed-in view of the conductive grid 404, in accordance with some embodiments. The conductive grid includes wires 406 and thermoplastic strain relief 402. The wires comprises conductive and flexible material that may be sealed or surrounded in an insulating material. The thermoplastic strain relief 402 is a flexible material between the wires that is not conductive. The thermoplastic strain relief 402 provides a minimum bend radius to prevent a wire stress fracture from bending or folding of the conductive grid 404.

Figure 5:
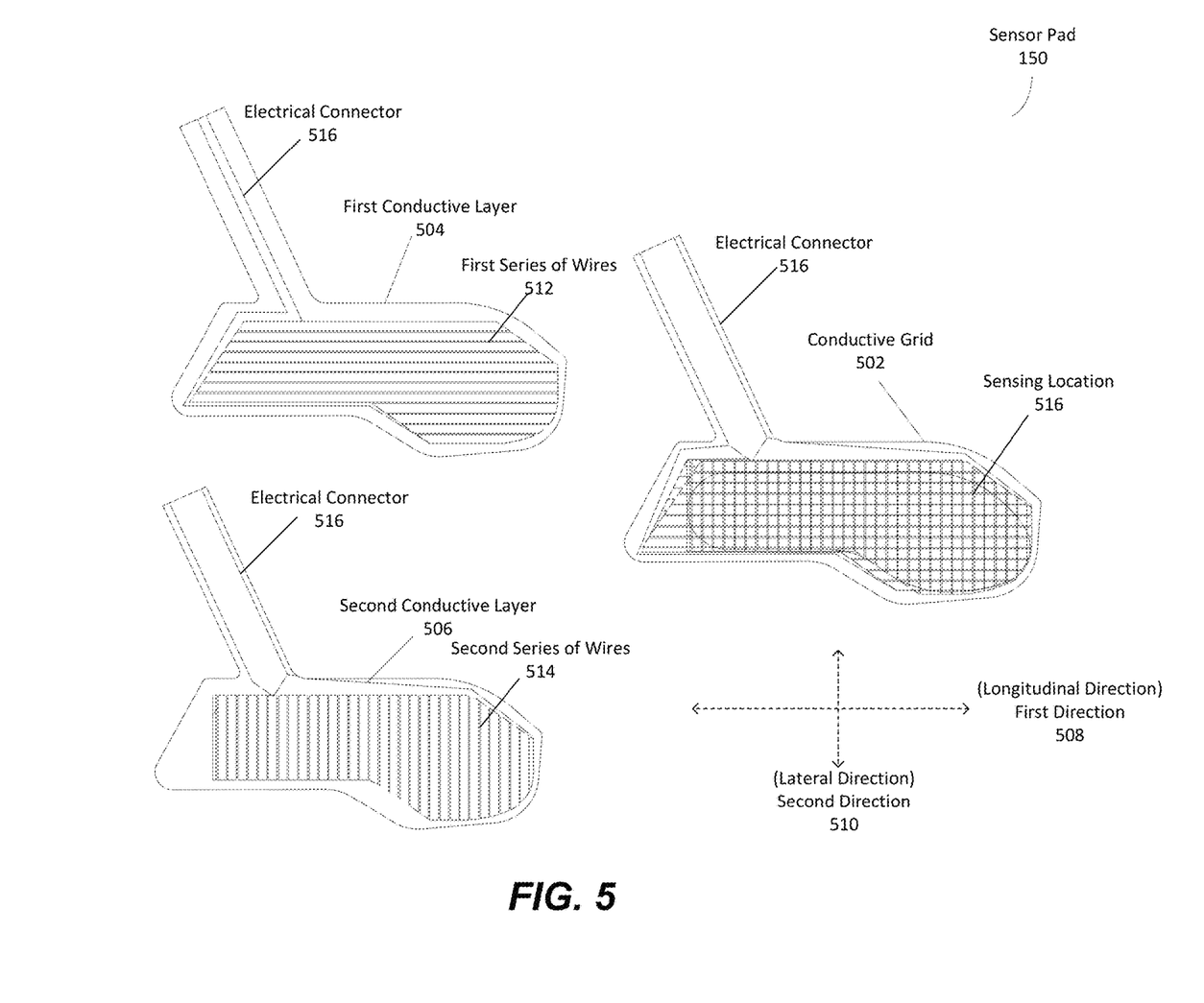
FIG. 5 includes various top views of a conductive grid in a sensor pad, in accordance with some embodiments.

FIG. 5 is an illustration of the layers of the conductive grid 502, in accordance with some embodiments. The conductive grid 502 of FIG. 5 is an example of conductive grid 404 that exhibits two conductive layers 504 and 506 on top of each other to form a grid of intersecting wires. The first conductive layer 504 is composed of a first series of wires 512 running parallel to each other in a first direction 508. The first conductive layer additional has an electrical connector 516 that may connect the sensor pad 150 to the wireless transmitter 140. The second conductive layer 506 is comprised of a second series of wires 514 running parallel to each other in a second direction 510 that is different from the first direction. The second conductive layer 506 may additionally have an electrical connector 516 connecting the sensor pad 150 to the wireless transmitter 140. The electrical connector 516 may be a wire, socket, flexible circuit, cable, or wireless transmitter. While the embodiment shown in FIG. 5 is a protruding member of the sensor pad, the electrical connector may also take another form. The first and second conductive layers 504 and 506 are coupled (e.g., overlayed on each other) such that the first series of wires 512 and second series of wires 514 create a conductive grid 502. The first and second series of wires 512 and 514 have their wires running in perpendicular directions (508 and 510) and thus form a grid of wire intersections. Each intersection comprises a sensing location at which a discrete value can be sensed. As such, the grid generates a matrix of pressure readings. Each intersection of the grid defines a coordinate in a two-dimensional pressure dataset. The first direction 508 and second direction 510 of the first and second series of wires do not have to be perpendicular. The first and second series of wires 512 and 614 may comprise any number of wires, with more wires providing more sensing locations and better sensing resolution.

Micro-Cuts

Micro-cuts in the stiffener layers 306 or shielding layers 304 may improve flexibility and conformability and prevent image artifacts associated with the pressure data, while improving sensor image quality. In some embodiments, the material of the stiffener and shielding layers 304 and 306 may have a low compressibility so as not to interfere with transmission of pressure to the sensor. Variations in cut pattern or density allow stiffness and conformability to vary in different regions of the sensor as needed. In some embodiments, the micro cuts take the form of cuts that do not penetrate through an entire layer of stiffener layer 306 or shielding layer 304. In other embodiments, the micro cuts may cut through one of the layers but not the other layer.

Figure 6:
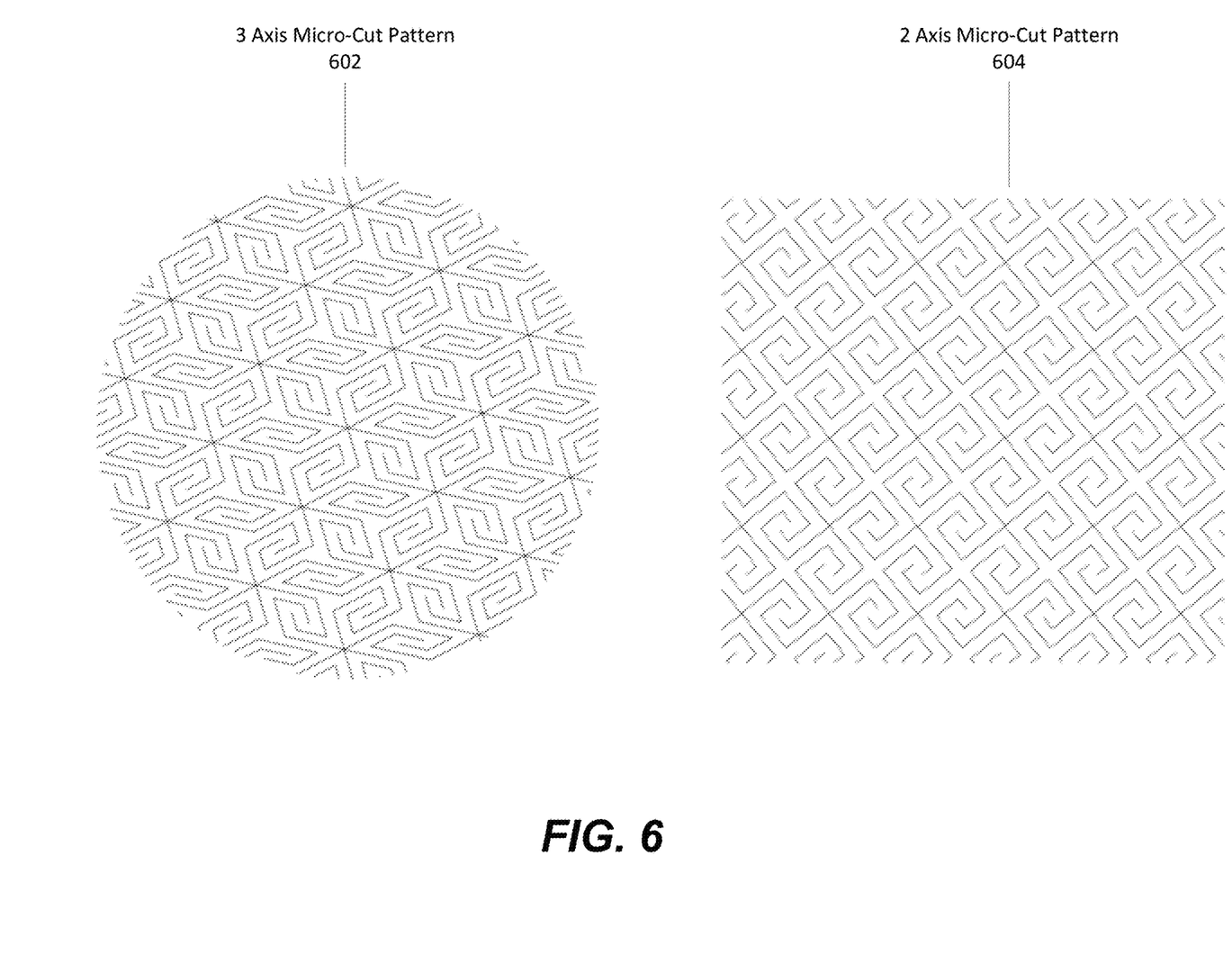
FIG. 6 includes conceptual diagrams of various examples of micro-cut patterns that may be applied to a sensor pad, in accordance with some embodiments.

FIG. 6 includes illustrations of micro-cut patterns 602 and 604 that may be marked into layers of the sensor pad in accordance with some embodiments. The micro-cut patterns 602 and 604 may be inscribed, cut, or otherwise etched onto the shielding 304 and stiffener 306 layers. The depth of the etching may be varied to vary flexibility of the etched layer such that, for example, a deeper etching may make the layer more flexible. Micro-cut patterns may be designed in a way that enables flexibility of the material in a one or more predefined directions 708. The 3 axis micro-cut pattern 602 enables flexibility of the material in 3 axes while the 2 axis micro-cut pattern 604 enables flexibility of the material in 2 axes. The one or more predefined directions 708 of flexibility can vary by changing the pattern or its orientation on the material of the layer. The micro-cut pattern reduces resistance of the stiffener layer in the one or more predefined directions 708 to enhance the sensor layer stretching or compressing in the one or more predefined directions 708 to conform with the contoured surface of the substrate.

A layer with the micro-cuts may provide structural support in the directions parallel to the shoe floor but offer lower or almost no resistance in the perpendicular direction. This is to prevent the structure of the sensor itself from absorbing any of the pressures being transmitted to the shoe floor. For example, imagine trying to wrap a sphere with a flat sheet of paper. The paper will need to be folded and overlapped because there is excess material with nowhere to go. The micro-cuts allow the wearable sensor pad to stretch or compress ever so slightly to conform to the shoe floor so that the wearable sensor pad is measuring the pressure which actually occurs at that interface. Creases or folds in the sensor would be measured as false pressures in the image. In another situation, if the sensor is too flexible, it can ball up underneath the foot during any walking/running motion. This may create folds in the sensor or produces contact between the wearer and the sensor that otherwise not have occurred if the sensor remained on the shoe floor, thus producing false pressures.

Figure 7:
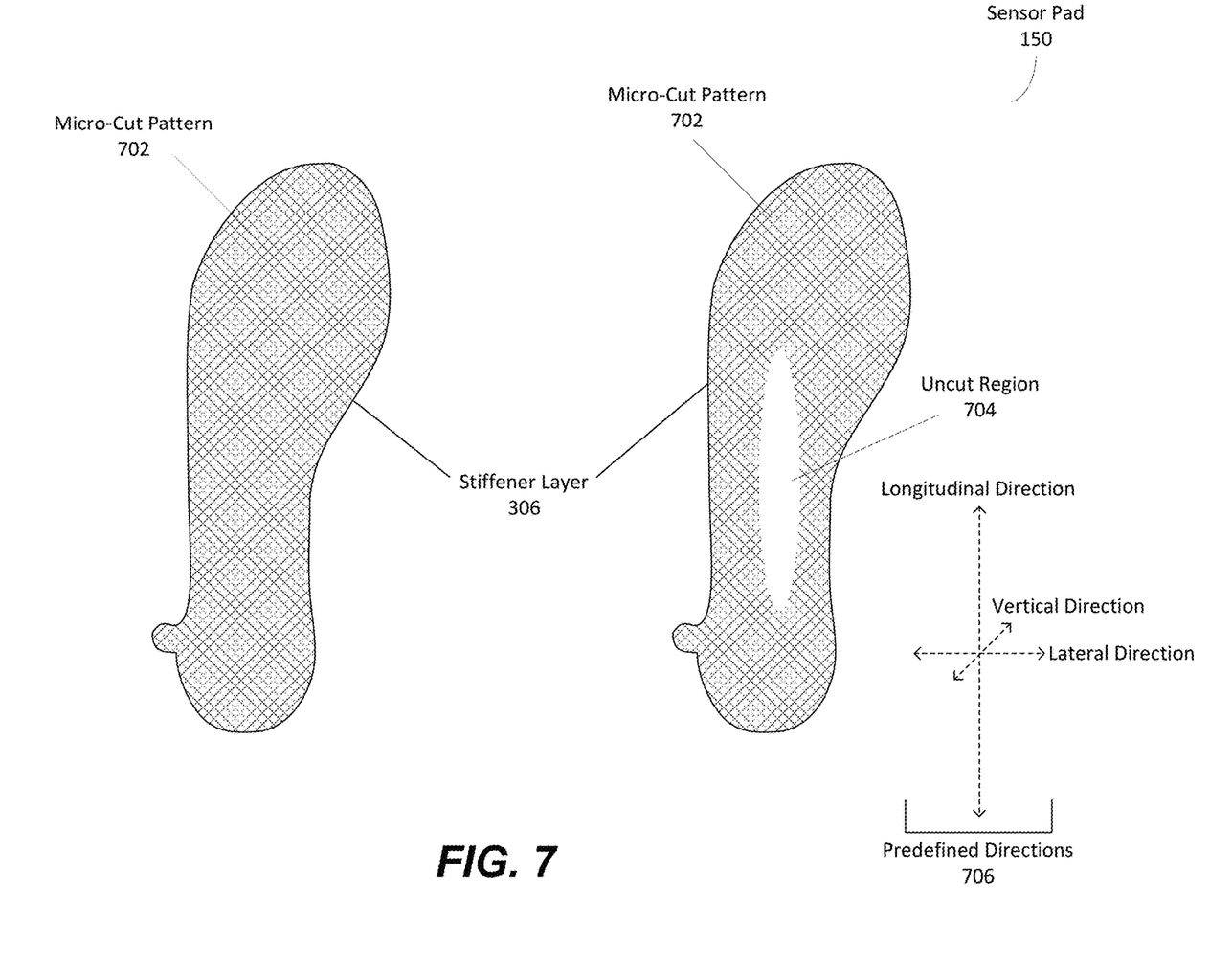
FIG. 7 is an illustration of micro-cut pattern placement on the sensor pad, in accordance with some embodiments.

FIG. 7 is an illustration of micro-cut pattern placement on the sensor pad in accordance with some embodiments. Depending on the embodiment, some layers of a sensor pad 150 may be etched with a micro-cut pattern 702 on the whole surface area of the layer, as seen on the left side of FIG. 7. However, other embodiments may only have a portion of the surface area of the layer etched with the micro-cut pattern 702 and the rest an uncut region 704. The uncut region 704 will not have the added flexibility of the region with the micro-cut pattern 702. In some embodiments having an uncut region 704 may be beneficial. For example, in the embodiment of the sensor pad 150 being an insole, the uncut region 704 may be placed under the arch of the foot where there is unlikely much compression on the sensor pad which decreased the need for flexibility and contouring to the foot or shoe surface. In other embodiments the sensor pad 150 may have different micro cut patterns 702 such as patterns 602 and 604 in different regions of the layer. Varying the micro-cut pattern 702 may allow for some regions to flex more than others as needed.

The stiffener layers are produced from a pre-prepared material stack-up of conductive fabric, lamination adhesive, and mylar plastic sheet in that order. The completed stack is then cut (laser-cut, die cut, etc.) into the sensor shape with the desired micro-cut pattern. This stack-up of materials acts as electronic shielding to improve recorded data while allowing flexibility for the wearable sensor pad to conform the contours of the shoe or other substrate and simultaneously ensuring the structural integrity of the sensor. This conformity allows the sensor to better stick to the shoe bottom rather than the wearer, thus improving comfort during use. The materials are of low compressibility as to not interfere with the transmission of pressure to the sensor.

Exemplary Configuration

Figure 8:
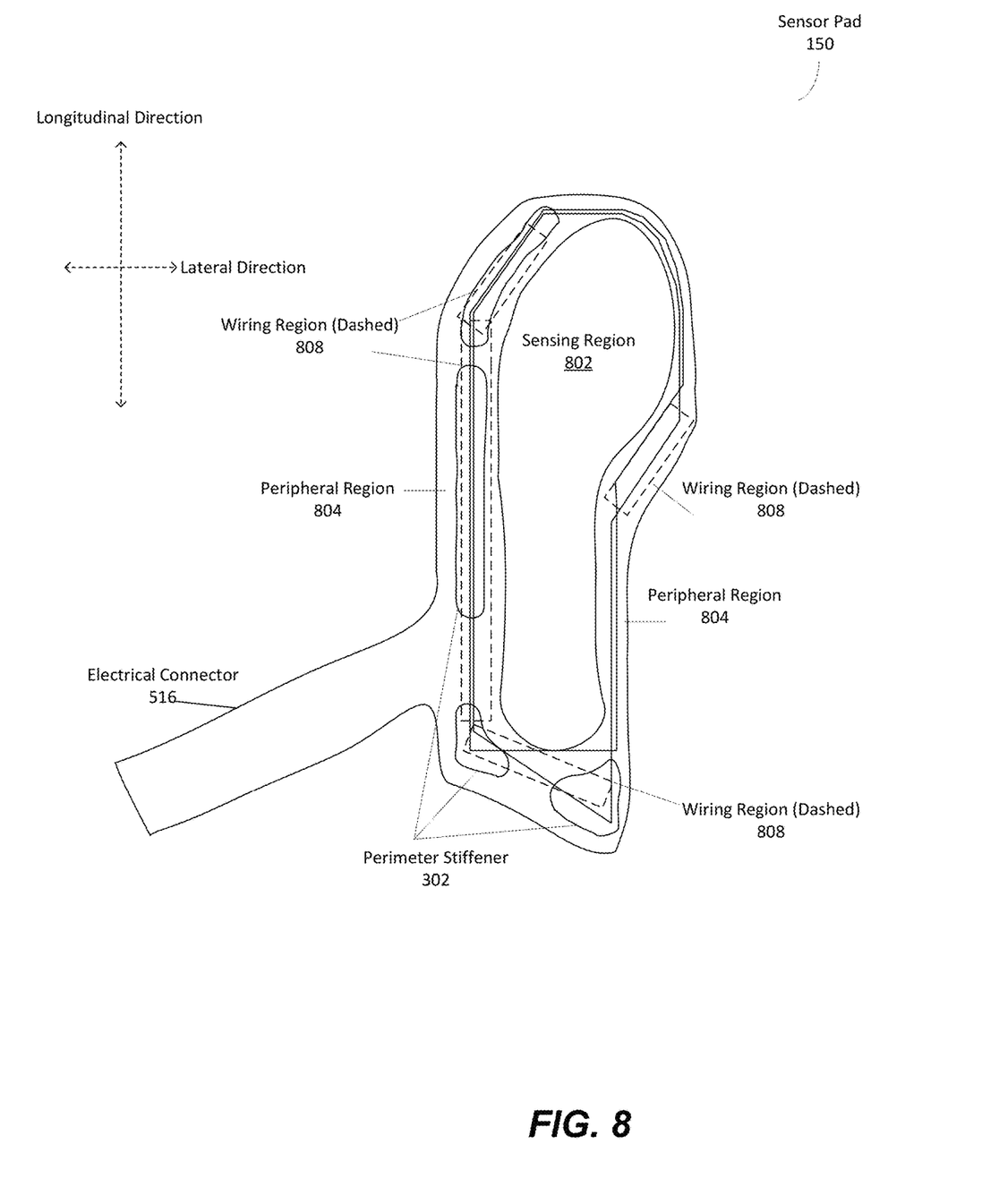
FIG. 8 is an illustration of the placement of various components of a sensor pad, in accordance with some embodiments.

FIG. 8 is an illustration of the placement of various components of a sensor pad 150 in accordance with some embodiments. In the shown embodiment the sensor pad 150 is in the form of an insole to be put in a shoe. The view shown in FIG. 8 shows a top down view of the placement of components of the sensor pad 150 as outlines. Note that the multiple layers shown in FIG. 3 are not shown here for simplicity. All of the components depicted in FIG. 8 are sealed in the flexible enclosure.

The foot shape at the center of the wearable sensor pad 150 is the sensing area 802 of the pad. The sensing area 802 may be comprised of conductive grid layers 308, wiring 310, and dielectric 312 with the conductive grid configured as shown in FIG. 5 to provide sensing locations. Shielding 304 and stiffener 306 layers are stacked on top of the layers making up the sensing area 802 to protect the electronics and provide structure to the sensor pad 150. The layers are then encapsulated by the flexible enclosure 301.

Beyond the edges of the sensing region 802 is the peripheral region 804. The peripheral regions are foldable upwards when the insole is inserted into a shoe and house the wiring 808 and electrical connectors of the sensor pad 150. Electrical wirings and bonding of the wirings with the conductive layers can be located outside of the sensing area 802 in the peripheral region 804 such that electrical connections 516 wrap up on side of the foot, without interfering with the sensor pad 150 fit. The conductive grid of the sensing area 802 may not extend into the peripheral region 804 such that the peripheral region 804 does not provide sensor data of the side portions of the foot.

The rigid perimeter stiffeners 302, which may be referred to as strain reliefs, may serve two or more purposes. First, the rigid perimeter stiffeners 302 define the folding and bending points of the wearable sensor pad. Second, rigid perimeter stiffeners 302 protect the electrical wiring that run along the perimeter of the wearable sensor pad from being mechanically damaged. The perimeter stiffeners 302 may be formed from a thermoplastic urethane material or a more rigid Mylar material. In various embodiments, the shape and number of pieces may vary.

Figure 9:
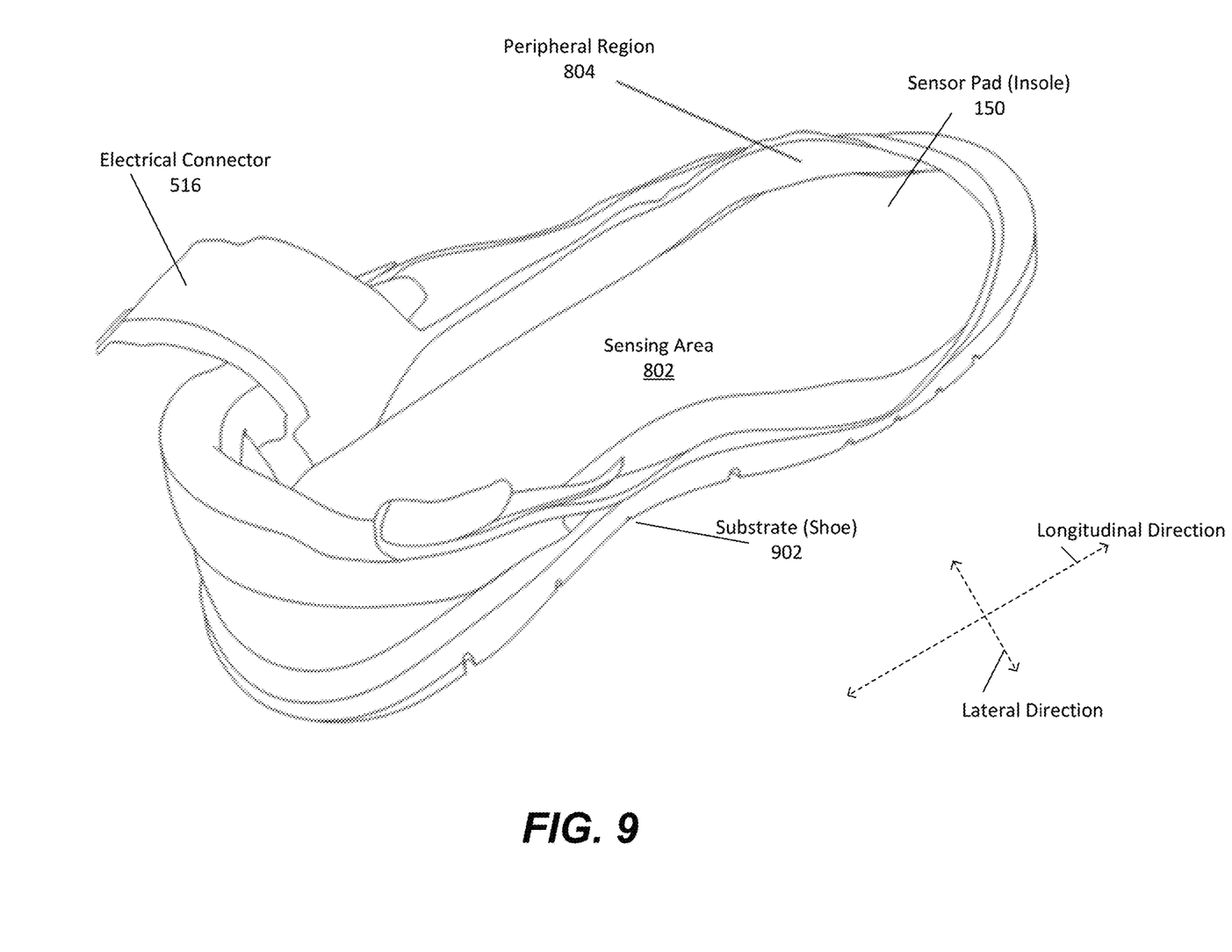
FIG. 9 is a perspective view of a sensor pad placed in a shoe, in accordance with some embodiments.

FIG. 9 is an illustration of the sensor pad 150 in a shoe 902 in accordance with some embodiments. In this embodiment, the substrate that the sensor pad 150, in the form of an insole, rests on is a shoe 902. The sensing area 802 is on the interior bottom of the shoe where a foot rests, while the peripheral region 804 is folded up along the interior side of the shoe. The electrical connector that couples the sensor pad 150 to a wireless transmitter 140 folds upward away from the sensing area 802 to wrap toward the leg of the user. In some embodiments the sensing area 802 may be in a variety of sizes to best fit the shoe and foot of the user without bending the sensing area 802.

Figure 10:
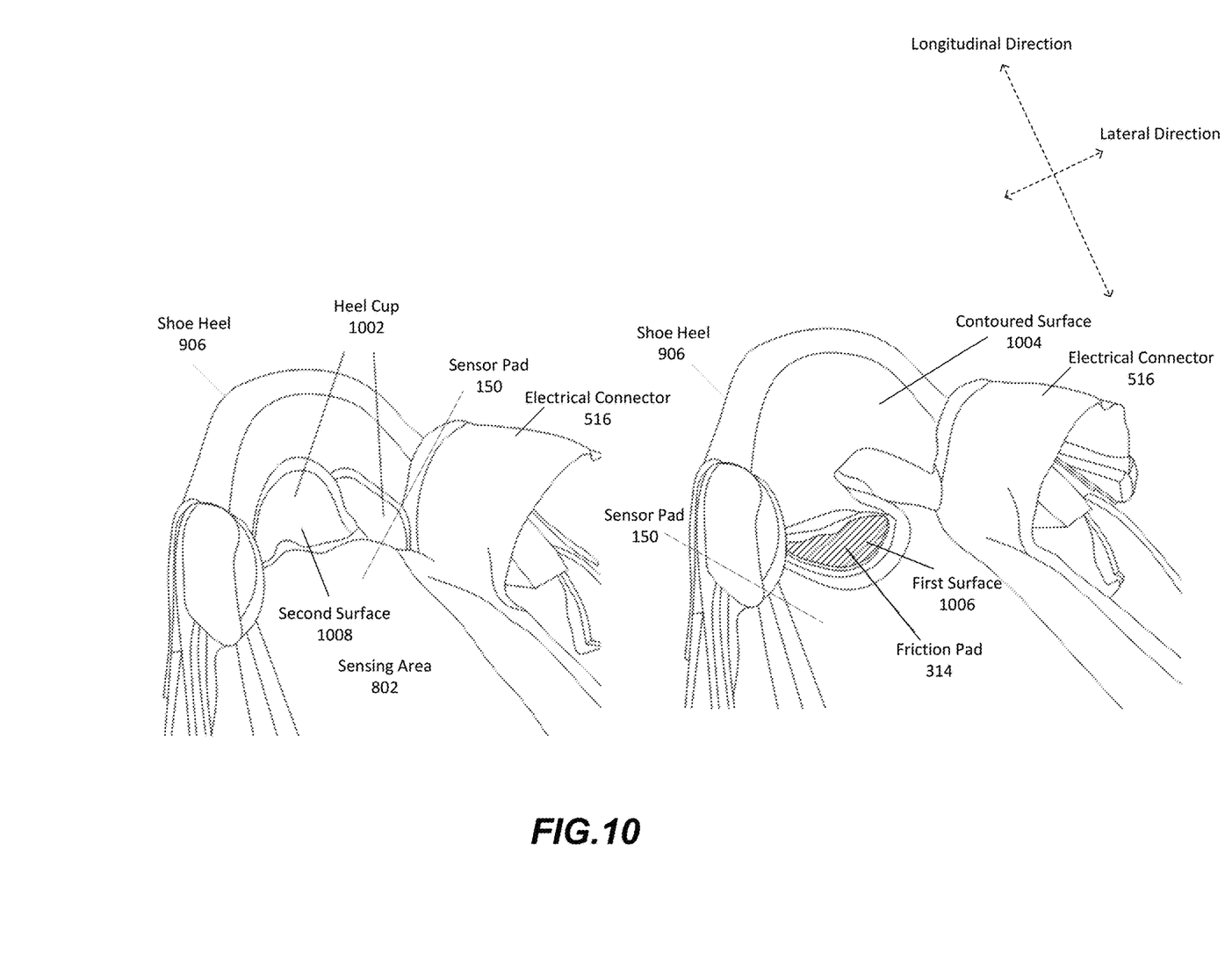
FIG. 10 includes zoomed-in views of the heel of a shoe in which a sensor pad is placed, in accordance with some embodiments.

FIG. 10 is a zoomed-in view of the heel 906 of a shoe in which the sensor pad 150 is placed in accordance with some embodiments. The interior of the shoe heel 906 has a contoured surface 1004 against which friction pads 314 of the sensor pad 150 rest. The friction pads 314 have a first surface 1006 that is textured to increase friction between the sensor pad 150 and the contoured surface 1004 to frictionally couple the two and prevent the sensor pad 150 from slipping in the shoe. The second surface 1008 of the friction pad 314 faces the interior of the shoe and comes into contact with the user's heel or Achilles tendon region. In some embodiments there are multiple friction pads 314. The multiple friction pads fold upward away from the sensing area 802 and flex to fit the contoured surface 1004 and form a heel cup 1002. The heel cup 1002 cradles the user's heel for comfort and stability of the sensor pad 150. The heel cup 1002 prevents movement of the sensor by providing a pocket for the heel. Friction pads 314 at the heel further prevent sensor movement and define how the heel folds to create a consistent heel cup each time.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not always imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. A wearable sensor pad comprising a sensing region and a peripheral region, the wearable sensor pad configured to be in contact with a substrate with a contoured surface, the wearable sensor pad comprising:
a sensor layer having a surface area that defines a sensing area, the sensor layer configured to measure values detected at a plurality of locations of the sensing area; and
a plurality of rigid stiffeners at predefined locations of the peripheral region of the wearable sensor pad, the rigid stiffeners configured to restrict a folding pattern of the wearable sensor pad, wherein the sensing region includes a majority of the sensing area of the sensor layer, the peripheral region is configured to be folded at an angle relative to the sensing region.

2. The wearable sensor pad of claim 1, wherein the wearable sensor pad is an insole and the substrate is a shoe.

3. The wearable sensor pad of claim 1, wherein the substrate is part of a human body.

4. The wearable sensor pad of claim 1, wherein the sensor layer forms a capacitance sensor and comprises a conductive layer and a dielectric layer.

5. The wearable sensor pad of claim 1, wherein the sensor pad comprises a flexible enclosure, a capacitive layer, a stiffener layer, wiring, and perimeter stiffeners.

6. The sensor pad of claim 1, further comprising one or more friction pads configured to be folded away from the sensing area and provide a textured surface to frictionally couple the sensor pad to a surface.

7. The sensor pad of claim 1, further comprising a conductive grid, the conductive grid comprising a series of wires each separated by a non-conductive thermoplastic material providing strain relief.

8. The sensor pad of claim 1, wherein the sensor layer comprises a conductive grid that comprises two conductive layers, a first conductive layer having a first series of wires arranged in a first direction and a second conductive layer having a second series of wires arranged in a second direction different from the first direction, the first and second conductive layer, when coupled, forming a plurality of discrete sensing locations at wire intersections of the first and second series of wires.

9. The sensor pad of claim 1, further comprising an electrical connector connecting the sensor pad to a wireless transmitter.

10. The sensor pad of claim 1, further comprising a stiffener layer that comprises a micro-cut pattern that reduces resistance of the stiffener layer in one or more predefined directions to enhance the sensor layer stretching or compressing in the one or more predefined directions to conform with the contoured surface, wherein the stiffener layer further comprises an uncut region lacking the micro-cut pattern, the uncut region configured to not be flexible along the predefined direction.

11. The sensor pad of claim 1, further comprising a peripheral region adjacent to the sensing area, the peripheral region configured to be folded away from the sensing area, the peripheral region comprises a perimeter stiffener.

12. An insole configured to be inserted into a shoe, the insole comprising:
  a flexible enclosure that is foldable;
  a sensor layer enclosed by the flexible enclosure, the sensor layer defining a sensing area shaped for the sole of a foot;
  a plurality of rigid stiffeners coupled to the flexible enclosure at predefined locations to define a folding pattern of the flexible enclosure, the flexible enclosure corresponding to at least a sensing region and a peripheral region, the sensing region including a majority of the sensing area of the sensor layer, the peripheral region is configured to be folded at an angle relative to the sensing region; and
  an electrical connector connected to the sensor layer at a point of connection that is located in the peripheral region.

13. The insole of claim 12, wherein the sensor layer is configured to measure signals corresponding to pressure exerted on the insole, and the peripheral region is configured to be folded to a location that experiences less pressure than the sensing region, thereby protecting wiring and the electrical connector.

14. The insole of claim 12, wherein the plurality of stiffeners comprises a stiffener layer having a shape of the sole of a foot, the stiffener layer having a micro-cut pattern on at least a portion of the stiffener layer, the micro-cut pattern enabling flexibility of the stiffener layer in a chosen direction.

15. The insole of claim 14, wherein the stiffener layer lacks the micro-cut pattern on a portion of the layer at one or more predefined locations.

16. The insole of claim 12, wherein the rigid stiffeners comprise one or more stiffener tabs configured to conform to a heel of the shoe.

17. The insole of claim 16 wherein the stiffener tabs comprise a first surface that is configured to contact an interior of the heel of the shoe and a second surface that is configured to contact the foot, the first surface contacting the interior of heel of the shoe having a texture for increasing friction between the insole and the interior.

18. A system comprising:
  a sensor pad configured to output sensor pad data, the sensor pad comprising a sensing region and a peripheral region, the sensor pad comprising:
    a sensor layer having a surface area that defines a sensing area, the sensor layer configured to measure values detected at a plurality of locations of the sensing area; and
    a plurality of rigid stiffeners at predefined locations of the peripheral region of the sensor pad, the rigid stiffeners configured to restrict a folding pattern of the sensor pad, wherein the sensing region includes a majority of the sensing area of the sensor layer, the peripheral region is configured to be folded at an angle relative to the sensing region;
  an application in communication with the sensor pad, the application comprising a user interface configured to:
    display a heatmap of a pressure differential across the sensor pad;
    display a gait visualization; and
    display a load graph of representing force exerted on the sensor pad.

19. The system of claim 18, wherein the user interface is configured to display statistics calculated from previous data stored by a server.

20. The system of claim 18, further comprising a wireless transmitter configured to transmit sensor pad data from the sensor pad to a server.

* * * * *